United States Patent [19]

Herrmann et al.

[11] Patent Number: 5,041,228

[45] Date of Patent: Aug. 20, 1991

[54] PROCESS FOR SEPARATING MIXTURES OF SUBSTANCES CONTAINED IN AN AQUEOUS OR AQUEOUS/ORGANIC SOLUTION

[75] Inventors: W. A. Herrmann, Giggenhausen; Jurgen Kulpe, Freising; Werner Konkol, Oberhausen; Hanswilhelm Bach; Wilhelm Gick, both of Duisburg; Ernst Wiebus, Oberhausen; Thomas Müller, Bochum; Helmut Bahrmann, Brünen, all of Fed. Rep. of Germany

[73] Assignee: Hoechst Aktiengesellschaft, Fed. Rep. of Germany

[21] Appl. No.: 373,097

[22] Filed: Jun. 28, 1989

[30] Foreign Application Priority Data

Jun. 30, 1988 [DE] Fed. Rep. of Germany ....... 3822036

[51] Int. Cl.$^5$ ............................................. B01D 15/08
[52] U.S. Cl. .................................. 210/656; 210/658; 502/22
[58] Field of Search .................... 210/656, 658; 502/22

[56] References Cited

U.S. PATENT DOCUMENTS

| | | | |
|---|---|---|---|
| 3,002,823 | 10/1961 | Flodin et al. | 210/656 |
| 4,248,802 | 2/1981 | Kuntz | 568/454 |
| 4,321,414 | 3/1982 | Costa | 568/862 |
| 4,504,588 | 3/1985 | Gärtner et al. | 502/24 |

FOREIGN PATENT DOCUMENTS 103845  3/1984  European Pat. Off. .

OTHER PUBLICATIONS

High Pressure Liquid Chromatographic Separations of Some Rhodium and Iridium Triphenylphosphine Complexes, Enos et al., Analytical Chemistry, vol. 48, No. 7, Jun. 1976.
Introduction to Modern Liquid Chromatography, Second Edition, Snyder et al., pp. 203-204, 1979.
Patent Abstracts of Japan, vol. 4, No. 149 (P-32) [631]. Oct. 21, 1980; JP-A-55-99068, 7/28/80, Patent Abstracts of Japan, vol. 7, No. 242 (C-192) [1387].
Oct. 27, 1983; JP-A-58-131,994, 8/6/83, Patent Abstracts of Japan, vol. 9, No. 32 (C-265) [1755].
Feb. 9, 1985, JP-A-59177133, 10/6/84.

*Primary Examiner*—Stanley S. Silverman
*Assistant Examiner*—Krisanne Shideler
*Attorney, Agent, or Firm*—Jordan B. Bierman

[57] ABSTRACT

Mixtures of substances containing metal complex compounds, organoelemental ligands, and/or other components are separated according to the invention by chromatography on stationary supports in an aqueous or aqueous/organic medium.

48 Claims, No Drawings

PROCESS FOR SEPARATING MIXTURES OF SUBSTANCES CONTAINED IN AN AQUEOUS OR AQUEOUS/ORGANIC SOLUTION

This Application claims the priority of German Application P 38 22 036.9, filed June 30, 1988.

The invention relates to a process for separating mixtures of substances containing metal complex compounds, organoelemental ligands, and other components in an aqueous or aqueous/organic solution by gel chromatography.

BACKGROUND OF THE INVENTION

Metal complex compounds are being used increasingly as catalysts in commercial processes. Important examples of reactions which are catalyzed by complex compounds are hydrogenation, hydroformylation, and polymerization. The metal complex compounds can be used alone, but frequently are combined with co-catalysts. In other cases they are employed in conjunction with excess ligands to increase their stability.

The hydroformylation process described in DE-PS 26 27 354 is an example of a reaction catalyzed by metal complex compounds. The catalyst system consists of a water-soluble rhodium complex with a water-soluble organic phosphane as a ligand and excess water-soluble phosphane. The water-solubility of the phosphane ligands is due to the presence of sulfonic acid groups in the molecule. They are preferably used in the form of alkali sulfonates, ammonium sulfonates, or alkaline earth sulfonates. The process particularly excels in its high selectivity towards the formation of straight-chain aldehydes. Furthermore, it avoids the formation of significant amounts of high-boiling by-products. For their use as catalysts, the compounds must often be available as pure metal complexes. Therefore, the manufacturing process must be followed by purification which is as efficient and loss-free as possible.

Furthermore, spent catalysts should be regenerated and reactivated in a simple manner. Thus, in the hydroformylation process described in DE-PS 26 27 354, the efficiency of the catalyst system in the formation of straight-chain aldehydes with high selectivity decreases over time with continuous operation or repeated use of the same catalyst solution.

This loss in selectivity has various causes; i.e. catalyst poisons, such as iron carbonyl, which result from the synthesis gas acting on the synthesis gas transport pipes or the reactor material, and the formation of undesired higher-boiling condensation products from the aldehydes. The selectivity is also reduced by the decrease in the ratio of phosphane to rhodium during prolonged use of the catalyst system; this is a result of degradation and oxidation processes to which the sulfonated phosphanes are subjected. These reactions lead, for example, to sulfonated phosphane oxides, phosphane sulfides, aromatic sulfonic acids, and disulfophenylphosphinic acid, in each case in the form of the respective salt. Moreover, rhodium-containing cluster compounds can also be produced. Similar conversion and degradation reactions are also observed when lipophilic catalyst systems are used; they contain arylphosphanes, e.g. triphenylphosphane, as ligands. Neither phosphane oxides, phosphane sulfides, nor the salts of aromatic sulfonic acids and disulfophenylphosphinic acid act as catalysts alone or together with rhodium. The same also applies to the cluster compounds of rhodium.

It is therefore appropriate to replace the aqueous catalyst solution which contains such cleavage products either partially or completely by fresh solution from time to time. Apart from the above-mentioned conversion and degradation products of the sulfonated phosphanes, the spent catalyst solution contains rhodium as a complex compound, as well as excess water-soluble salts of sulfonated phosphanes and impurities which are brought in with the reactants. To ensure the cost effectiveness of the process, it is desirable to recover both the rhodium complex and the excess active phosphanes.

The purification of metal complex compounds as part of the manufacturing process and the regeneration of metal complex compounds used as catalysts are the subjects of various publications. A process for recovering catalyst systems containing water-soluble rhodium compounds, sulfonated organic phosphanes, and cations is described in DE 32 35 029 A1. In this process, an amount of acid at least equivalent to the acid groups present is first added to the aqueous solution of the catalyst system. Then extraction is performed with an amine which is dissolved in an organic solvent. The organic phase, containing the amine salt of the sulfonated phosphane, is separated and treated with an aqueous solution of an inorganic base, such as NaOH.

The inactive conversion and degradation products of the sulfonated triarylphosphane can be removed by adjusting the pH to a suitable value. An aqueous solution of the phosphane sulfonate and rhodium complex is obtained which can be reused as a catalyst solution either directly, after dilution with water, or after the addition of sulfonated phosphane. This process always provides a mixture of the rhodium complex and the excess ligand. Selective separation of the rhodium complex and the other components is therefore possible only to a limited extent.

DE-OS 19 12 380 relates to a process for separating, by the use of cellulose membranes, coordination complexes of transition metals from a homogeneous free-flowing mixture of complexes with one or more organic components. This procedure is also used to separate rhodium complex compounds from mixtures which contain the reaction products from hydroformylation of low molecular weight olefins in a homogeneous phase. The rhodium complex compounds are insoluble in water and no excess ligands are present. Separation is limited to splitting the mixture into the rhodium compound and the other components, in particular olefins and aldehydes.

Aqueous solutions, containing rhodium complex compounds and water-soluble ligands in addition to other components, can also be recovered using membranes by reverse osmosis, ultrafiltration, or microfiltration. In this manner, about 50% of the salts contained in the solution can be separated, while 99% of the complex-bound rhodium is retained. Apart from the required extreme dilution of the feed solution, another disadvantage of this procedure is that some of the unchanged ligands are also lost with the precipitated salts and must be recovered in an additional process step.

Although sulfonated and thus water-soluble phosphanes were first reported as complex ligands 30 years ago by Chatt et al. J. Chem. Soc. (1958) 276; ibid. (1958) 1403, metal complexes of such ligands have hardly been investigated to date and only a few have been manufactured. The main reason for this is that no separating and purification processes for water-soluble complexes of this type have been available so far. For this reason, in spite of the efficiency of the hydroformylation process described in DE-PS 26 27 354, other commercial processes with sulfonated phosphanes as a catalyst component have not been able to establish themeselves, nor has the chemical industry been able to develop complex compounds containing water-soluble phosphanes as ligands. A literature search provides impressive substantiation of this situation. Wilkinson et al (Nouv. J. Chim. 2 (1978) 137) reports on water-soluble complexes of the ligand $(C_6H_5)_2P(m-C_6H_4SO_3Na)$ which, however, sometimes occur as hydrates and whose structures have not been conclusively established.

The experiments conducted by Patin et al (Tetrahedron Lett. 28 (1987) 2507) on the synthesis of the triphenylphosphane trisulfonate derivative $ClRh[P-(C_6H_4-m-SO_3Na)_3]$, which has an analogous formula to the known complex $ClRh[P(C_6H_5)_3]_3$, resulted in a mixture of several compounds. This meant that it was impossible to define the catalytic activity of the individual components in the hydrogenation of unsaturated carboxylic acids. The fact that the method inherently involves the formation of phosphane oxide $O=P(C_6H_4-m-SO_3Na)_3$ seems to be particularly prejudicial to catalysis (Patin, l.c. and J. Mol. Catal. 44 (1988) 191).

A recent dissertation on the synthesis of organonickel complexes of trisulfonated triphenylphosphane also failed for lack of a method to separate the reaction products (A. Sivade, Ph. D. thesis dated 11/13/87, Université Paul Sabatier, Toulouse, France).

Therefore, the problem was to develop a process for the separation of the components of an aqueous solution containing metal complex compounds, free ligands, and other compounds in as simple a manner as possible. This process is to permit both the purification e.g. of metal complex compounds and organoelemental ligands and the regeneration of catalyst systems with metal complex compounds as active components.

DESCRIPTION OF THE INVENTION

The invention consists of a process for separating mixtures of substances containing metal complex compounds, organoelemental ligands, and/or other components in an aqueous or aqueous/organic solution. It is characterized in that the mixture of substances is separated by chromatography on water-resistant gels.

Gel chromatography, which is also called gel permeation or size-exclusion, chromatography, is a technique used particularly in polymer chemistry and biochemistry to separate compounds with high molecular weights e.g. polymer mixtures, proteins, and saccharides.

Surprisingly, it has been found that gel chromatography is also admirably suitable for separating compounds whose molecular weights are much lower than those of polymeric and biological materials. A particularly remarkable feature is that even molecules whose molecular weights differ only minimally can be separated. Sulfonated triphenylphosphane and sulfonated triphenylphosphane oxide, for example, may be separated from each other, even though the difference in their molecular weights is only about 3%. This is evidence of the fact that, in contrast to the principle of gel chromatography known in the literature ("size exclusive only"), when the claimed process is used, separation is not only according to molecular size, but also substrate/support interactions have a considerable effect thereon.

It was also not to be expected that the complex compounds in the stationary phase would not be subject to decomposition and conversion reactions. Even air and heat-sensitive organometallic complex compounds can be easily purified using the new procedure, and mixtures containing such compounds can be separated into their components without any difficulty.

According to the claimed process, the porous materials conventionally employed for gel chromatography are used as stationary solid phases. However, in contrast to known applications, they are not selected mainly according to the molecular weight or the molecular volume of the substances to be separated, but in particular according to the substance type to be separated. Basically, all gels which are stable in the aqueous medium are suitable. These include polysaccharides, which can optionally be modified, such as dextran and agarose; silica gels; polyethyleneglycol dimethylacrylate; styrene gels cross-linked with divinylbenzene; porous glass; and polyacrylamides. Modified organic polymers are particularly suitable. The dextrans cross-linked with epichlorohydrin (marketed under the name Sephadex) and oligoethylene glycol-glycidyldimethacrylatepentaerythritol dimethacrylate copolymers (marketed under the name Fractogel) have proved to be particularly valuable.

The liquid phase principally serves as a transport medium or mobile solvent for the substances to be purified or the mixtures of substances to be separated. Generally, the solvent for the mixture of substances and the eluent are the same. In special cases, it is recommended that different liquids be used. Water and mixtures of water and organic solvents are suitable. Of the organic solvents, compounds containing hydroxyl groups have proved their worth, in particular low molecular weight alcohols, i.e. those with up to 5 carbon atoms such as methanol and ethanol as well as tetrahydrofuran. The selection of a suitable solvent or solvent mixture depends on the solubility of the substances to be treated. If necessary, preliminary tests can be carried out to determine what solvents and solvent combinations can be used. In the special case presented here, solvation phenomena must be taken into consideration; the mobile solvents used (such as water and methanol) can be greatly influenced in their behaviour by additional complexing of the coordination and complex compounds to be separated. Such effects are insignificant in the applications of gel chromatography known in literature.

Above all, temperature and flow rate as well as column packing all have influence on the quality of the separation. Normally, temperatures ranging from 0° to 95° C., in particular 10° to 50° C. and preferably 15° to 35° C. are employed. When aqueous solutions are used as the mobile phase, it is advantageous to work with temperatures of at least 10° C., while temperatures below 10° C. are preferred when solvent mixtures are used.

A constant diameter over the length of the columns used is also very important if a clean separation of the individual zones from each other is to be achieved.

The flow rate is understood to be the volume of solution in cc which passes through the gel bed per cm$^2$ of column cross section per hour. Normally, the flow rate is 0.5 to 40 cc$\times$cm$^{-1}$. When pressure is applied, the flow rate can be greatly increased. Low flow rates of 0.5 to 5 cc$\times$cm$^{-2}\times$h$^{-1}$ improve separation of the components. Flow rates of 2 to 4 cc$\times$cm$^{-2}\times$h$^{-1}$ are preferred.

As mentioned previously, the claimed process can also be used under pressure, although the pressureless embodiment is preferred. Pressures of 0.5 to 10 MPa and in particular 1 to 6 MPa can be used. The precondition for working under pressure is the use of gels which are pressure-stable.

The substances to be purified or separated are added to the stationary phase as solutions. Apart from the substances to be treated and their impurities, these solutions can contain other inorganic or organic compounds. If, for example, the catalyst phase of a hydroformylation process according to DE-PS 26 27 354 is to be treated, the aqueous solution can contain, not only the catalytically active complex compound, free ligand, and conversion and degradation products of the ligands, but also salts such as sodium chloride and organic substances such as aldehyde and alcohols.

The concentration of all dissolved substances can be 10 to 50% by weight and is, in particular, below 20% by weight. The limit is determined by the viscosities of the solutions to be separated and thus also depends on the solvent. The viscosity of the solutions is also the reason the flow rates are low at the beginning of separation. Only when the sample becomes increasingly diluted during the course of chromatography can the flow rate be increased.

The amount of solution added to the stationary phase depends on the column volume. It has proved valuable to select the solution volume so that it is 1% to 20% of the volume of the column.

The complex compounds to be purified or separated according to the claimed process contain organoelemental ligands and are soluble in water. Organoelemental ligands are understood to be aryl compounds of the elements phosphorus, arsenic, antimony, and bismuth. Their water-solubility is achieved by the introduction of sulfonate ($SO_3^-$) and/or carboxylates ($COO^-$) groups. Thus, the organoelemental ligands can be described by the following general formula:

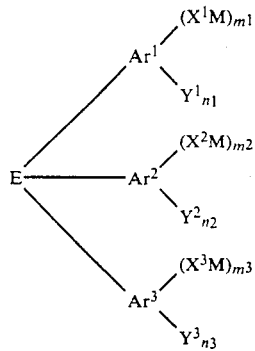

In this formula E stands for phosphorus, arsenic, antimony, or bismuth; $Ar^1$, $Ar^2$, and $Ar^3$ are each phenyl or naphthyl; $Y^1$, $Y^2$, and $Y^3$ each denote straight or branched chain alkyl each independently having 1 to 4 carbon atoms, alkoxy each having 1 to 4 carbon atoms, halogen, OH, CN, $NO_2$, or $R^1R^2N$, in which $R^1$ and $R^2$ stand for straight or branched chain alkyl each independently having 1 to 4 carbon atoms; $X^1$, $X^2$, and $X^3$ are each carboxylate ($COO^-$) or sulfonate ($SO_3^-$); $n_1$, $n_2$, and $n_3$ are each an integer from 0 to 5; M is an alkali metal ion, the equivalent of an alkaline earth metal or zinc ion, or an ammonium or quaternary alkyl ammonium ion of the general formula $N(R^3R^4R^5R^6)^+$, in which $R^3$, $R^4$, $R^5$ and $R^6$ are each a straight or branched chain alkyl group having 1 to 18 carbon atoms. Quaternary ammonium groups in which three of the groups $R^3$, $R^4$, $R^5$ and $R^6$ each contain 1 to 4 carbon atoms and the fourth group contains 1 to 18 carbon atoms have proved particularly useful. Each of $m^1$, $m^2$, and $m^3$ is an integer from 0 to 3, at least one of $m^1$, $m^2$ or $m^3$ is equal to or greater than 1.

The complex compounds are derived from metals of the so-called subgroups (groups 3-12) of the Periodic Table of the Elements. Apart from the organoelemental ligands, they can also contain other complex components. Examples of such ligands are: CO, $CO_2$, $C_2H_4$, HC≡CH, $S_x(x \geq 1)$, halogen, and NO.

The claimed process can be used both in the laboratory and on a pilot or production plant scale. In practice, columns, in particular glass or plastic columns, are used as reactors, and the gel is located therein on permeable plates. The column length is only limited as to a minimum length of at least 5 cm, preferably 60 to 120 cm. Inhomogeneities in the column packing with long column bodies can be overcome by dividing a single large column into short individual columns in sequence. The column diameter can be freely selected and, for laboratory experiments, it is preferably between 0.5 and 10 cm. With industrial applications, diameters of 1 meter or more are achievable with present-day technology.

Gel chromatography permits the dissolved substances to be fractionated according to their molecular weights. As already mentioned above, interactions of the complex ligands with reactive groups (such as carboxyl or hydroxy) of the gels must be involved to a considerable extent in the separation of the mixtures of substances according to the claimed process. Therefore, it is possible to obtain a sharp separation of the desired solution components from each other, even though this would not be expected with pure exclusion effects.

When spent aqueous catalyst solutions are used, the catalytically active complex compound and the excess ligand can be separated free of foreign components and returned to the catalyst cycle. Therefore, on a commercial scale, the claimed process is particularly suitable for continuous operation. In this case, the catalyst solution to be regenerated and containing degradation products which are damaging to the process is removed from a sidestream of the catalyst cycle. For recovery, it is fed into a separating unit consisting of one or more columns. The columns are filled with gel as the stationary phase and with water. The gel is freed from adherent air by suitable measures such as backrinsing and evacuation.

After the first column of a separating unit consisting of several columns has been charged, the system switches over automatically to the next column, and then the other columns in sequence. The columns charged with the catalyst solution are eluted with water to separate the solution components. The fractions containing the catalytically active complex and/or free ligands are recirculated into the catalytic process via a collective line under elevated pressure, if necessary. In general, it is not necessary to treat the separating column with washing water before a new regeneration cycle. Overall, the amounts of elution water and washing water (if required), which are reused in the process, can be selected so that they correspond to the amount of water removed with the product. The process not only permits the separation of degradation products which damage the process, but also the removal of activity-reducing cluster compounds.

The detection of the separated components takes place in known manner, the simplest being by the use of an UV-fluorescent lamp, with automatic operation preferably by wavelength-variable UV spectroscopy, refractometry, and infrared spectroscopy. The last detection method mentioned is particularly successful with carbon monoxide complexes, as such complexes exhibit very intensive CO stetching vibrational bands.

The following examples illustrate the process according to the invention. Naturally, it is not intended to restrict the invention to these special embodiments.

The abbreviations used in the examples have the following meanings:

TPPTS: trisodium triphenylphosphane trisulfonate
TPPDS: disodium triphenylphosphane disulfonate
TPPOTS: trisodium triphenylphosphane oxide trisulfonate
TPPODS: disodium triphenylphosphane oxide disulfonate
TPPSTS: trisodium triphenylphosphane sulfide trisulfonate

EXAMPLE 1

Separation of the Components of a Spent Catalyst Solution

This Example describes the treatment of an aqueous solution containing a rhodium carbonyl complex and water-soluble phosphanes, in particular TPPTS as free ligands and conversion products of these ligands, in addition to other components. The solution has been used as a catalyst in the hydroformylation of olefins.

Sephadex G-15, which has previously been treated with degassed, nitrogen-saturated water, is used as the stationary phase. The gel is a 95 cm long packing in a column with a diameter of 40 mm. 100 ml of solution are introduced. Elution takes place with water, the solvent flow is 21 $cc \times cm^{-2} \times h^{-1}$. Four fractions are obtained whose retention times are listed in Table 1. The retention times reflect the maxima of absorption at $\lambda$—330 nm.

TABLE 1

| Fraction | Retention Time (min) |
| --- | --- |
| 1 | 295 |
| 2 | 477 |
| 3 | 577 |
| 4 | 603 |

The fractions are characterized by phosphorus-NMR spectroscopy, field desorption mass spectroscopy (measurement of the negative ion stream), and HPLC analysis.

Water-soluble phosphane is found in Fraction 4, water-soluble phosphane oxide and other P(V) compounds in Fraction 3. Fraction 2 contains the catalytically active complex H(CO)Rh(TPPTS)$_3$ in addition to small amounts of water-soluble phosphane. Other rhodium-phosphane complexes are contained in Fraction 1, as the NMR spectroscopic analysis shows (coupling of the rhodium to the phosphorus nucleus).

EXAMPLE 2

Example 1 is repeated except that 150 ml of solution are introduced and the solvent flow is increased to 32 $cc \times cm^{-2} \times h^{-1}$. The components of the solution can still be separated perfectly even under these conditions which are more severe than those of Example 1.

TABLE 2

| Fraction | Retention Time (min) |
| --- | --- |
| 1 | 131 |
| 2 | 229 |
| 3 | 261 |
| 4 | 293 |

The fractions obtained are spectroscopically identical to those of Example 1.

EXAMPLE 3

Purification of ClRh(TPPTS)$_3$

In order to prepare the compound of ClRh(TPPTS)$_3$, RhCl$_3$.3H$_2$O, dissolved in water, is reacted with excess TPPTS, which is also dissolved in water. The Rh(III) is reduced to Rh(I) by the phosphane which converts to the corresponding phosphane oxide. In addition, the reaction product also contains small amounts of phosphane sulfide. To remove the excess TPPTS and the by-products TPPOTS and TPPSTS, 10 ml of the reaction solution (containing approximately 3 g of TPPTS, 1.2 g of TPPOTS, and a little TPPSTS) is treated in the column described in Example 1. The rhodium complex compound is eluted in pure form at a solvent flow rate of 7 $cc \times cm^{-2} \times h^{-1}$ after a retention time of 424 minutes (absorption at $\lambda = 330$ nm).

EXAMPLE 4

Separation of a solution containing H(CO)Rh(TPPTS)$_3$

This Example describes the separation into its components of an aqueous solution containing the rhodium complex (H(CO)Rh(TPPTS)$_3$, as well as NaCl, NaOH, TPPTS, TPPDS, TPPOTS, TPPODS, and formaldehyde. The dry residue from the solution is 200 mg/cc.

a) When a 60 cm long column packed with Sephadex G-25 Superfine (length of gel packing: 25.5 cm) with a diameter of 2 cm is used at a feed rate of 1 cc of sample solution and a solvent flow rate of 2.8 $cc \times cm^{-2} \times h^{-1}$, the pure complex is obtained after a retention time of 353 minutes. The low molecular compounds are eluted after 572 minutes (these figures refer to the maxima of UV absorption at $\lambda$—473 nm).

b) 2 cc of the solution used in Example 4a) are treated in a 120 cm long column packed with Fractogel TSK HW 409 fine (length of gel packing): 91.5 cm) with a diameter of 2.4 cm. At a solvent flow rate of 4.5 $cc \times cm^{-2} \times h^{-1}$), the pure complex is obtained after a retention time of 505 minutes. The low molecular weight compounds are eluted after 675 minutes (these figures refer to the maxima of UV absorption at $\lambda = 340$ nm).

EXAMPLE 5

Purification of TPPTS

The Example shows the applicability of the new process for purifying substances at a very high solvent flow rate.

The solution used is the aqueous solution obtained in the manufacture of TPPTS by the sulfonation of triphenylphosphine with oleum. It contains approximately 28% by weight of TPPTS, 2.5% by weight of TPPDS, as well as the corresponding phosphane oxides, phosphane sulfides, and small amounts of other impurities originating from the sulfonation.

In order to recover pure TPPTS, 50 cc of the solution are introduced into the column described in Example 1. The solvent flow rate is 54 cc×cm$^{-2}$×h$^{-1}$. Five fractions are obtained which are listed, together with their retention times, in Table 3.

TABLE 3

| Fraction | Retention Time (min) |
|---|---|
| 1 | 85 |
| 2 | 123 |
| 3 | 159 |
| 4 | 201 |
| 5 | 268 |

The fractions are examined in the same manner as the starting solution by HPLC analysis and $^{31}$P-NMR spectroscopy. Despite the high solvent flow rate, TPPTS is obtained in Fraction 4 in a purity of more than 95% (determined by NMR and HPLC analysis). In this connection it deserves special mention that the TPPTS is free from the corresponding phosphane oxide which is either impossible to remove or can only be insufficiently removed by known processes.

What we claim is:

1. A process for the separation of metal complexes and/or organoelemental ligands from aqueous or aqueous/organic solutions thereof wherein said solutions are subjected to size-exclusion chromatography on water-resistant gels.

2. The process of claim 1 wherein said chromatography is carried out on a stationary phase in the presence of a mobile liquid phase.

3. The process of claim 2 wherein said stationary phase is water-resistant and is taken from the class consisting of polysaccharides, derivatives thereof modified; silica gels; polyethylene glycol dimethylacrylate; styrene gels cross-linked with divinylbenzene; porous glass, and polyacrylamides.

4. The process of claim 3 wherein said stationary phase is dextran and/or agarose.

5. The process of claim 2 wherein said stationary phase is a cross-linked organic polymer.

6. The process of claim 2 wherein said stationary phase is dextran cross-linked with epichlorohydrin.

7. The process of claim 2 wherein said liquid phase is also a solvent for said mixture.

8. The process of claim 2 wherein said liquid phase comprises water or a combination of water and organic solvents.

9. The process of claim 8 wherein said organic solvent contains hydroxyl groups.

10. The process of claim 9 wherein said organic solvent contains a low molecular weight alcohol having 1 to 5 carbon atoms.

11. The process of claim 8 wherein said organic solvent is taken from the class consisting of methanol, ethanol, tetrahydrofuran, and mixtures thereof.

12. The process of claim 11 wherein said organic solvents are taken from the class consisting of methanol, ethanol, and mixtures thereof.

13. The process of claim 8 wherein said liquid phase is water and said chromatography is carried out at a temperature of at least 10° C.

14. The process of claim 8 wherein said liquid phase is said combination and said chromatography is carried out at a temperature below 10° C.

15. The process of claim 2 wherein said chromatography is carried out at a temperature of 0° to 95° C.

16. The process of claim 15 wherein said temperature is 10° to 50° C.

17. The process of claim 16 wherein said temperature is 15° to 35° C.

18. The process of claim 2 wherein said chromatography is carried out in a column having a substantially constant diameter over its length.

19. The process of claim 18 wherein said chromatography is carried out at a flow rate of 0.5 to 40 cc per cm$^2$ of cross-section of said tube per hour.

20. The process of claim 19 wherein said flow rate is 0.5 to 5 cc per cm$^2$ per hour.

21. The process of claim 20 wherein said flow rate is 2 to 4 cc per cm$^2$ per hour.

22. The process of claim 2 wherein said chromatography is carried out at a pressure of 0.5 to 10 MPa.

23. The process of claim 22 wherein said pressure is 1 to 6 MPa.

24. The process of claim 22 wherein said pressure is super atmospheric and said stationary phase is pressure stable.

25. The process of claim 2 wherein said mixtures are added to said stationary phase as solutions.

26. The process of claim 25 wherein said mixtures are the result of a hydroformylation reaction and said solutions contain at least one of conversion and degradation products of said ligands, salts, and organic substances.

27. The process of claim 25 wherein said mixtures are the result of hydroformylation and said solutions contain at least one of conversion and degradation products of said ligands, sodium chloride, aldehydes, and alcohols.

28. The process of claim 25 wherein said solutions have a total concentration of all dissolved materials of 10% to 50% by weight.

29. The process of claim 25 wherein said solutions have a total concentration of all dissolved materials of less than 20% by weight.

30. The process of claim 25 wherein said chromatography is carried out in a column having a column volume and said solutions have a solution volume of 1% to 20% of said column volume.

31. The process of claim 2 wherein said ligands are aryl compounds of phosphorous, arsenic, antimony, and bismuth.

32. The process of claim 31 wherein said ligands contain sulfonate and/or carboxylate groups.

33. The process of claim 2 wherein said ligands are of the formula

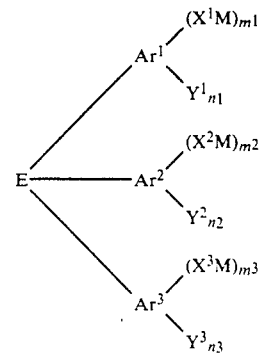

wherein E is phosphorus, arsenic, antimony, or bismuth; $Ar^1$, $Ar^2$, and $Ar^3$ are each phenyl or naphthyl; $Y^1$, $Y^2$, and $Y^3$ each denote straight or branched chain alkyl each individually having 1 to 4 carbon atoms, alkoxy each individually having 1 to 4 carbon atoms, halogen, OH, CN, $NO_2$, or $R^1R^2N$, in which $R^1$ and $R^2$ stand for straight or branched chain alkyl each individually having 1 to 4 carbon atoms; $X^1$, $X^2$, and $X^3$ are each carboxylate ($COO^-$) or sulfonate ($SO_3^-$); $n_1$, $n_2$, and $n_3$ are each an integer from 0 to 5; M is an alkali metal ion, the equivalent of an alkaline earth metal, a zinc ion or equivalent thereof, or an ammonium or quaternary alkyl ammonium ion of the general formula $N(R^3R^4R^5R^6)+$, in which $R^3$, $R^4$, $R^5$ and $R^6$ are each a straight or branched chain alkyl group having 1 to 18 carbon atoms; each of $m^1$, $m^2$, and $m^3$ is an integer from 0 to 3, at least one of $m^1$, $m^2$ or $m^3$ being equal to or greater than 1.

34. The process of claim 2 wherein said complexes are of metals of Groups 3 to 12 of the Periodic Table of the Elements.

35. The process of claim 2 wherein said ligands also include CO, $CO_2$, $C_2H_4$, HC≡CH, $S_x$(X 1), halogen, NO, or mixtures thereof.

36. The process of claim 2 wherein said chromatography is carried out in at least one column, said stationary phase being on permeable plates therein.

37. The process of claim 36 wherein said column is glass or plastic.

38. The process of claim 36 wherein said column has a minimum length of 5 cm.

39. The process of claim 38 wherein said length is 60 to 120 cm.

40. The process of claim 36 wherein said column has an internal diameter of at least 0.5 cm.

41. The process of claim 40 wherein said internal diameter is 0.5 to 10 cm.

42. The process of claim 40 wherein said internal diameter is about 1 meter.

43. The process of claim 2 wherein said metal complexes are catalysts in a catalytic reaction, are removed from said reaction in the form of said mixture, and are returned to said catalytic reaction after said chromatography.

44. The process of claim 43 wherein said catalysts are returned to said catalytic reaction under pressure.

45. The process of claim 2 wherein said stationary phase is oligoethylene glycol-glycidyldimethacrylate-pentaerythritol dimethacrylate.

46. The process of claim 2 wherein said stationary phase is a water-resistant gel.

47. The process of claim 1 wherein said solutions are the reaction products of metal complex catalyzed hydrogenation, hydroformylation, or polymerization.

48. The process of claim 1 wherein said solutions contain free ligands, degradation products thereof, salts, and organic substances.

* * * * *